United States Patent [19]

Dundas et al.

[11] Patent Number: 4,692,701

[45] Date of Patent: Sep. 8, 1987

[54] METHOD OF TESTING STEAM TURBINE ROTORS TO DETERMINE IF THEY SHOULD BE RETIRED BECAUSE OF EMBRITTLEMENT

[75] Inventors: Robert E. Dundas, Duxbury; Fred W. Tatar, Dedham, both of Mass.

[73] Assignee: Factory Mutual Research, Norwood, Mass.

[21] Appl. No.: 681,280

[22] Filed: Dec. 13, 1984

[51] Int. Cl.[4] .................... G01N 27/82; G01B 7/24
[52] U.S. Cl. ............................... 324/240; 324/209; 73/DIG. 2; 73/801
[58] Field of Search .............. 324/202, 209, 260–262, 324/233, 234, 236, 237, 238, 239, 240; 73/650, 659, 578, 577, 801, DIG. 2, 862.36, 862.69

[56] References Cited

U.S. PATENT DOCUMENTS

| | | | |
|---|---|---|---|
| 3,427,872 | 2/1969 | Leep et al. | 73/88.5 |
| 3,544,890 | 12/1970 | Bridges et al. | 324/226 |
| 3,588,683 | 6/1971 | Lloyd | 324/232 |
| 3,681,970 | 8/1972 | Wells | 73/656 X |
| 3,783,370 | 1/1974 | Birdwell et al. | 324/243 |
| 3,841,149 | 10/1974 | Edwin et al. | 73/659 |
| 4,112,353 | 9/1978 | Thompson | 324/54 |
| 4,126,491 | 11/1978 | Karlsson | 324/240 X |
| 4,290,016 | 9/1981 | Lorenz | 324/202 X |
| 4,309,903 | 1/1982 | Ono | 73/587 |
| 4,352,065 | 9/1982 | Rogachev et al. | 324/238 |
| 4,460,869 | 7/1984 | Buser et al. | 324/227 X |

FOREIGN PATENT DOCUMENTS

| | | |
|---|---|---|
| 2247634 | 9/1972 | Fed. Rep. of Germany . |
| 532803 | 2/1977 | U.S.S.R. ................ 324/209 |

OTHER PUBLICATIONS

Ono et al, "Magnetomechanical Acoustic Emission of Iron and Steels", *Material Evaluation*, Jan. 1980, pp. 55–61.

Karjalainen et al, "Detection of Plastic Deformation . . . of Barkhausen Noise", *NDT International*, Apr. 1979, pp. 51–55.

Bhattacharya et al, "A New Method of Detecting Fatigue . . . Ferromagnetic Specimens", *Journal of Testing and Eval.*, 7/1975, pp. 289–291.

Pasley, "Barkhausen Effect–An Indication of Stress", *Materials Evaluation*, 7/1970, pp. 157–161.

O. Sundstrom and K. Torronen, *Materials Evaluation*, Feb., 1979, "The Use of Barkhausen Noise Analysis in Nondestructive Testing", pp. 51–56.

L. P. Karjalainen, M. Moilanen, and R. Rautioaho, *Materials Evaluation*, Aug., 1979, "Influence of Tensile and Cyclic Loading Upon Barkhausen Noise in a Mild Steel", pp. 45–51.

*Primary Examiner*—Reinhard J. Eisenzopf
*Assistant Examiner*—Warren S. Edmonds
*Attorney, Agent, or Firm*—Lane & Aitken

[57] ABSTRACT

In a method for testing steam turbine rotors for embrittlement to determine which rotors to retire and which rotors to continue in operation, a varying magnetic field is applied to the rotor in a waveform to produce a detectable Barkhausen effect in the flux density developed in the rotor. The resulting Barkhausen burst of pulses is detected and is displayed on an oscilloscope. In addition, the pulse amplitude distribution of the pulses in the burst is plotted. The oscilloscope display and the pulse height distribution curve are compared with corresponding representations of the Barkhausen effect produced from a test sample known not to be embrittled, or from the rotor itself at a previous time, to make a determination of whether the rotor has become embrittled and whether to continue operation of the rotor.

8 Claims, 5 Drawing Figures

METHOD OF TESTING STEAM TURBINE ROTORS TO DETERMINE IF THEY SHOULD BE RETIRED BECAUSE OF EMBRITTLEMENT

BACKGROUND OF INVENTION

This invention relates to a method of nondestructive testing of steam turbine rotors and more particularly to a method of testing rotors to make a determination of whether the material of the rotor has become embrittled to a point where the rotor should be retired.

Steam rotors are subject to progressive embrittlement during operation at elevated temperatures as a result of the migration of impurities, such as antimony and arsenic, to the grain boundaries in the steel. These impurities form compounds, which weaken the grain boundaries creating zones of brittleness, which become subject to crack development. The progressive embrittlement could eventually lead to failure of the rotor, which can occur in a massive fracture during operation with catastrophic results, including tremendous property loss and loss of life. In the past there have been a number of major fractures of steam turbine rotors, which fractures can be attributed to this phenomenon of progressive embrittlement. At the present time there is no satisfactory way of testing the rotors for this condition of embrittlement. The inspection systems presently employed are sonic bore testing, in which ultrasonic waves are applied to the rotor bore, visual inspection for cracks, and taking test coupons from some location on the rotor and destructively testing the rotor material thus obtained. The problem is that neither of the first two methods test for the condition of embrittlement. The sonic bore testing and visual inspection will indicate the presence of cracks or other abnormalities in the steel structure, but embrittlement can occur without these abnormalities and the abnormalities can and do exist in rotors, which have not yet become excessively embrittled. Test coupons will give an indication of whether the part of rotor from which they are taken has become embrittled, but they should be taken only from places on the rotor remote from where embrittlement is likely to occur and thus fail to provide a reliable test for embrittlement. As a result there is a great deal of uncertainty as to when a steam turbine rotor should be retired. Because of the cost of the rotors, there is a considerable reluctance upon the part of the users to scrap a rotor, even when cracks are detected in the rotor. One rationalization or procedure employed by the turbine users to justify keeping a rotor in operation after a rotor flaw is detected is to keep track of the number of cold starts of the rotor after the flaw has been detected and make the decision whether or not to retire the rotor only after a number of cold starts have been experienced by the rotor. However, this procedure assumes that the eventual failure of the rotor would be caused by low cycle fatigue rather than embrittlement, as the progressive embrittlement of the rotor is not substantially affected by the number of cold starts of the rotor. The present uncertainty as to when is the proper time for a rotor to be retired has led to the situation in which the users of the rotors are continuing to operate their old rotors, even though the manufacturers of these rotors recommend that they be retired.

SUMMARY OF THE INVENTION

The present invention provides a solution to the problem of determining when a rotor has become excessively embrittled to the point where it should be retired. In accordance with the present invention, the rotor is subjected to a Barkhausen testing technique, in which a magnetic field is applied to the rotor in a sloped waveform. The resulting Barkhausen pulses during the magnetization are detected. Because the embrittlement is a grain boundary effect, the Barkhausen pulses produced from an excessively embrittled rotor will be different from those from a rotor which is not embrittled. In accordance with the invention, the Barkhausen pulses are applied to a pulse height analyzer and a graph is plotted, giving the distribution of the Barkhausen pulses by pulse heights. This graph is then compared with the distribution produced from a normal steel without embrittlement to determine the presence of embrittlement. In addition, the Barkhausen pulses are applied to an oscilloscope to produce a graph of the pulses as they are produced with time as the magnetization field applied to the rotor is increased. This time distribution of pulses is then compared with the distribution from normal steel, which is not embrittled. A difference in the time reproduction of the pulses by the oscilloscope will also represent an embrittled rotor. If the comparison indicates the rotor is embrittled, the rotor is retired from service.

Accordingly, an object of the present invention is to provide a nondestructive technique of determining when a steam turbine rotor has become embrittled.

A further object of the present invention, is to provide a technique to determine if progressive embrittlement of a steam turbine rotor has reached the point at which the rotor should be retired.

A further object of the present invention is to avoid catastrophic failure of steam turbine rotors.

Further objects and advantages of the present invention will become readily apparent as the following detailed description of the invention unfolds and when taken in conjunction with the drawings.

DESCRIPTION OF A PREFERRED EMBODIMENT

In accordance with the present invention, steam turbine rotors in operation are periodically shut down and dismantled and subjected to testing by applying a magnetic field to the rotor in a manner to generate a time distributed Barkhausen noise burst and then this burst is analyzed and compared with the Barkhausen noise from a rotor or rotor steel test sample known to be in good condition. The standard Barkhausen burst, with which the burst produced from the rotor under tests is to be compared, could for example, come from the same rotor when it was first installed or it could come from a test sample of the rotor steel, which test sample is known not to be embrittled. It is contemplated that the method of the present invention will be employed to test many turbine rotors which are now in operation and have been in operation for many years, and for these rotors it will be necessary to generate a standard Barkhausen burst from a test sample of the rotor steel for each rotor to be tested. The magnetization of a rotor and the detection of the Barkhausen noise burst is carried out on each part of the rotor which may be subject to embrittlement.

Figure 1:
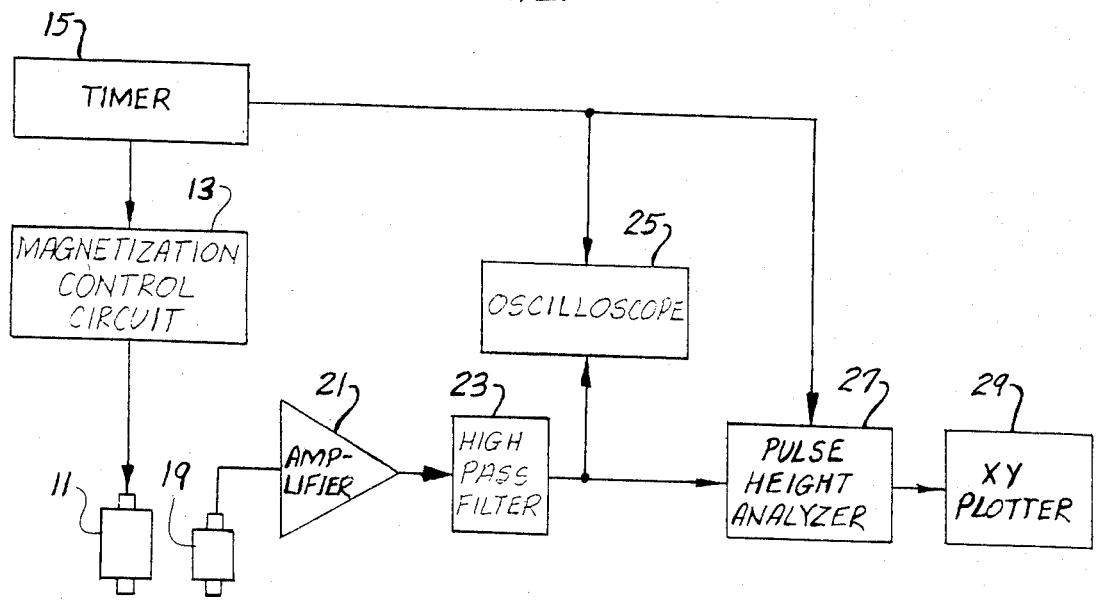
FIG. 1 illustrates the apparatus employed in the present invention to test the turbine rotors by the Barkhausen effect.
Figure 2:
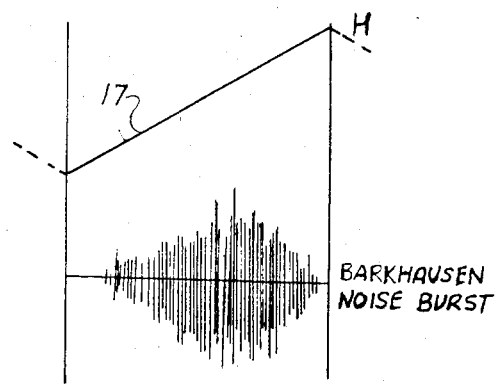
FIG. 2 is a graph showing the variation in the magnetic field as it is applied to the rotor during the test and an example of the resulting Barkhausen noise burst that could be produced by the magnetic field.

The equipment for carrying out the test in accordance with the present invention is illustrated in FIG. 1. As shown in FIG. 1, a magnetizing coil 11 is provided to apply a magnetic field to the turbine rotor or to the test sample to produce the standard burst for comparison. The magnetization coil is energized by a control circuit 13, which under the control of a timer 15 applies current in the form of a saw-tooth waveform to the coil 11 so that the applied magnetic field generated by the coil 11, and applied to the rotor or the test sample, has a shape of a saw-tooth waveform as illustrated by the curve 17 in FIG. 2. As shown in FIG. 2, the applied magnetic field, called the H field, has a waveform that, during one half cycle thereof, starts from a negative value and proceeds linearly to an equal and opposite positive value. The saw-tooth waveform then reverses to return to the negative value and cyclically repeats. As the applied magnetic field is increased linearly from the negative value toward the maximum positive value, a magnetic flux B is generated in the rotor or test sample. Microstructurally, this involves a reorientation of the magnetic domains in the material to line up with the applied magnetic field. Each domain switches its orientation individually. As each domain switches, a step change in the magnetic flux density B occurs, and a noiselike signal is produced. This noiselike signal is detected by a detector coil 19, which is positioned adjacent to the magnetization coil 11. Each step change in the magnetic flux density will cause the detection coil 19 to produce a pulse. Accordingly, as the applied magnetic field is changed linearly from the maximum negative value to the maximum positive value, a burst of time-distributed pulses is generated, each pulse being produced by the switching of the alignment of a magnetic domain. This burst of pulses is known as the Barkhausen effect. In FIG. 2 the curve 20 represents a typical time distributed burst of Barkhausen pulses, shown on the same time scale as the applied magnetic field wave form 17, which caused the Barkhausen burst to be produced.

Figure 3:
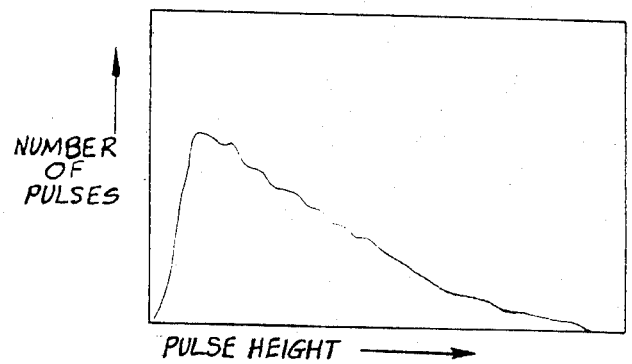
FIG. 3 is a typical distribution curve by pulse height for a typical Barkhausen noise burst.
Figure 4:
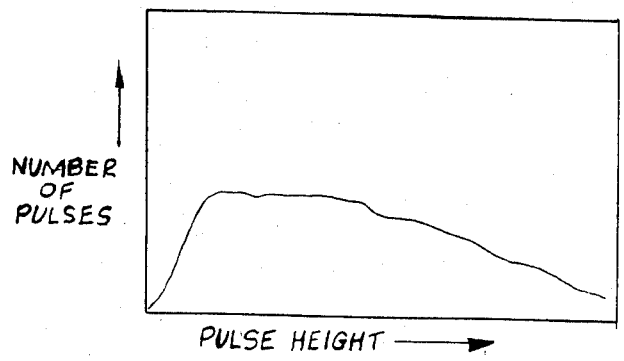
FIG. 4 is another distribution curve by pulse height for a Barkhausen noise burst.
Figure 5:
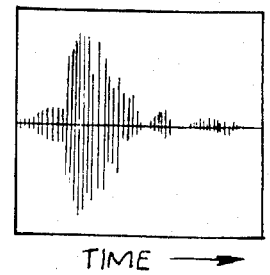
FIG. 5 is a graph of another Barkhausen noise burst plotted against time that can be produced.

In the apparatus employed in the invention, the Barkhausen pulses generated by the coil 19 are amplified by an amplifier 21 and then applied through a high pass filter 23 to an oscilloscope 25, which under the control of the timer 15, reproduces the time-distributed burst of Barkhausen pulses on the screen thereof for observation. In addition, the output pulses from the high pass filter 23 are fed to a pulse height analyzer 27, which controls an XY plotter 29 to produce a plot of the distribution of the pulses by amplitude during a selected part of the time interval, as the applied magnetic field is being increased linearly from the maximum negative value to the maximum positive value, and thus, of a selected part of the Barkhausen burst that is produced. The timer 15 signals the pulse analyzer 27 when to start and stop the time interval, during which the pulse height analysis takes place. A typical pulse height distribution curve produced by the XY plotter 29 for a typical Barkhausen burst is illustrated in FIG. 3. The plot of the pulse height distribution produced by the XY plotter 29 and or the pulse time distribution displayed on the oscillograph 25 produced from the rotor being tested is compared with the corresponding curve produced from a test sample of the rotor steel, or from same rotor when it was installed. If a marked change in pulse height distribution or in the pulse time distribution is observed, this will indicate that the rotor has become embrittled. For example, the pulse height distribution might change from that illustrated in FIG. 3 for the rotor or a test sample with no substantial embrittlement to that illustrated in FIG. 4, when the rotor has become embrittled. The pulse time distribution of the Barkhausen burst could change from that illustrated in FIG. 2 for a rotor or test sample with no substantial embrittlement to that illustrated in FIG. 5, when the rotor has become embrittled. In this manner the condition of the rotor having become embrittled can be readily determined, and the rotor is retired from service or continued in operation based on this determination.

The present invention provides a nondestructive and relatively inexpensive method of testing steam turbine rotors for embrittlement and thus, provides a rational basis for making a decision when each rotor should be retired. Accordingly the catastrophe of a massive fracture in operation may be avoided. The above description is of a preferred embodiment of the invention and modification may be made thereto without departing from the spirit and scope of the invention, which is defined in the appended claims.

What is claimed is:

1. A method of testing a steam turbine rotor in order to avoid failure of said rotor comprising testing said steam turbine rotor for embrittlement, wherein said embrittlement testing includes subjecting portions of the steam turbine rotor which may become embrittled to a magnetic field varying over a time interval with a predetermined waveform to generate a magnetic flux in said rotor and cause a detectable Barkhausen effect in said magnetic flux, said Barkhausen effect being characterized by step changes in said magnetic flux, generating pulses in response to said step changes in magnetic flux and comparing the Barkhausen effect as represented by the pulses produced from said rotor with Barkhausen data obtained from a test sample.

2. A method of testing a steam turbine rotor as recited in claim 1, wherein said embrittlement testing further includes generating a waveform representing the amplitude of said pulses distributed with respect to time as said pulses are generated in response to the variation of said magnetic field.

3. A method of testing a steam turbine rotor as recited in claim 2, wherein said embrittlement testing further includes producing a graph representing the distribution of said pulses by pulse amplitude.

4. A method of testing a steam turbine rotor as recited in claim 1, wherein said embrittlement testing further includes producing a graph representing a distribution of said pulses by pulse amplitude.

5. A method of testing a steam turbine rotor as recited in claim 1, wherein said embrittlement testing further includes applying a magnetic field varying over a time interval with said predetermined waveform to a test sample made of the same steel as said rotor to generate a magnetic flux in said test sample and cause a detectable Barkhausen effect in said test sample magnetic flux, said test sample Barkhausen effect being characterized by step changes in magnetic flux, and generating a burst of pulses in response to the step changes in magnetic flux density occurring as a result of the variation in the magnetic field applied to said test sample.

6. A method of testing a steam turbine rotor as recited in claim 1 wherein said waveform represents a linear variation in the applied magnetic field.

7. A method of using a steam turbine rotor and retiring said rotor from service if it becomes embrittled, comprising applying a magnetic field to a test sample varying over a time interval with a predetermined waveform to generate a magnetic flux in said test sample and cause a detectable Barkhausen effect in the flux density passing through said test sample, said Barkhausen effect being characterized by step changes in said magnetic flux density, and generating pulses in response to the step changes in said magnetic flux density occurring as a result of the variation of the magnetic field applied to said test sample; applying a magnetic field varying over a time interval with said waveform to portions of said rotor which may become embrittled to generate a magnetic flux in said rotor and cause a detectable Barkhausen effect in the flux density passing through said rotor, said Barkhausen effect being characterized by step changes in said magnetic flux density, and generating pulses in response to the step changes in flux density passing through said rotor; comparing the Barkhausen effect as represented by the pulses produced from said rotor with the Barkhausen effect as represented by the pulses produced from said test sample; and retiring said rotor or continuing said rotor in operation based on such comparison.

8. A method of using a steam turbine rotor and retiring said rotor from service if it becomes embrittled, comprising, applying a magnetic field when said rotor is first installed to portions of said rotor which may become embrittled when said rotor is first installed, over a time interval with a predetermined waveform to generate a magnetic flux in said rotor and cause a first detectable Barkhausen effect in the flux density passing through said rotor, said Barkhausen effect having characterized by step changes in said magnetic flux density, and generating pulses in response to the step changes in said flux density in said first Barkhausen effect, occurring as a result of the variation of the magnetic field applied to said rotor; then at a later time, after said rotor has been in use, applying a magnetic field with said waveform to said rotor to generate a magnetic flux in said rotor and cause a second detectable Barkhausen effect in said rotor, said Barkhausen effect being characterized by step changes in said magnetic flux density, and generating pulses in response to the step changes in flux density in said second Barkhausen effect; comparing the second Barkhausen effect as represented by the pulses produced from said rotor with the first Barkhausen effect as represented by the pulses produced from said rotor; and retiring said rotor or continuing said rotor in operation based on such comparison.

* * * * *